(12) United States Patent
Rosenberg (10) Patent No.: US 6,530,931 B1
(45) Date of Patent: Mar. 11, 2003

(54) NON-CONTAMINANT RECHARGEABLE, POWERED AND MANUAL DERMATOME

(75) Inventor: Lior Rosenberg, Omer (IL)

(73) Assignee: L.R.R. & D. Ltd., Omer (IL)

( * ) Notice: Subject to any disclaimer, the term of this patent is extended or adjusted under 35 U.S.C. 154(b) by 0 days.

(21) Appl. No.: 09/701,814
(22) PCT Filed: Jun. 3, 1999
(86) PCT No.: PCT/IL99/00296
§ 371 (c)(1), (2), (4) Date: Feb. 13, 2001
(87) PCT Pub. No.: WO99/62412
PCT Pub. Date: Dec. 9, 1999

(30) Foreign Application Priority Data

Jun. 4, 1998 (IL) ................................................ 124762

(51) Int. Cl.⁷ ............................................. A61B 17/42
(52) U.S. Cl. ........................ 606/132; 606/131; 606/167
(58) Field of Search ............................. 606/131–132, 606/167

(56) References Cited

U.S. PATENT DOCUMENTS

| | | | |
|---|---|---|---|
| 2,457,772 A | | 12/1948 | Brown et al. |
| 2,579,029 A | | 12/1951 | Barker et al. |
| 3,412,732 A | * | 11/1968 | Simon ........................... 30/209 |
| 3,428,045 A | | 2/1969 | Kratzsch et al. |
| 3,631,595 A | * | 1/1972 | Scott et al. ...................... 30/45 |
| 3,670,734 A | | 6/1972 | Hardy, Jr. ..................... 128/305 |
| 4,083,102 A | * | 4/1978 | Harshberger ..................... 30/45 |
| 4,091,880 A | | 5/1978 | Troutner et al. ............. 173/163 |
| 4,690,139 A | | 9/1987 | Rosenberg ................ 128/305.5 |
| 4,754,756 A | * | 7/1988 | Shelanski ..................... 606/132 |
| 4,838,284 A | * | 6/1989 | Shelanski .................... 128/898 |
| 4,917,086 A | | 4/1990 | Feltovich et al. ........... 606/132 |

FOREIGN PATENT DOCUMENTS

| | | | | |
|---|---|---|---|---|
| DE | 29 16 268 B 1 | | 4/1979 | |
| DE | 29 16 739 B 1 | | 4/1979 | |
| WO | WO 98/06144 | * | 2/1998 | ............ H01M/2/02 |

* cited by examiner

*Primary Examiner*—Aaron J. Lewis
*Assistant Examiner*—Linh Truong
(74) *Attorney, Agent, or Firm*—Anderson Kill & Olick; Eugene Lieberstein; Michael N. Meller (57) ABSTRACT

Mechanically actuated dermatome comprising a cutting blade, a hollow handle substantially perpendicular to the plane of the cutting blade and a motor housed in the hollow handle with its shaft substantially perpendicular to the plane of the cutting blade. The cutting blade is enclosed in a housing which has a lowermost surface that rides on the skin during treatment, the lower surface being essentially parallel to the plane of the cutting part of the blade and the handle is substantially perpendicular to it and directed upwards when the dermatome rests on the lowermost surface of the blade housing. The lowermost surface that rides on the skin during treatment is smooth, without any protrusion that may interfere with its movement in any direction with respect to the skin.

5 Claims, 9 Drawing Sheets

NON-CONTAMINANT RECHARGEABLE, POWERED AND MANUAL DERMATOME

FIELD OF THE INVENTION

This invention relates to dermatomes, useful for surgical operations such as skin grafting and tangential excision, particularly to dermatome wherein the cutting blade may also be actuated for a reciprocal motion by mechanical means, usually comprising electrical motor means.

BACKGROUND OF THE INVENTION

Dermatomes, used for surgical operations and particularly for skin-grafting purposes, are known in the art. They comprise a cutting blade, which reciprocates in a direction essentially perpendicular to the direction of advancement of the dermatome, and handle means or the like for controlling and displacing the dermatome as required. The blade may be actuated in its reciprocating motion, either manually or by mechanical means, which are usually electrical or gas turbine motor means. A suitable electrical power or gas supply source is provided, and usually is a central source connected to said motor means by cables or tubes, as the case may be.

U.S. Pat. No. 2,579,029 describes a dermatome with a manually reciprocated knife coupled with suction means for drawing the skin to be cut closely against the cutting blade, the length of the cut being limited by the width of the suction means and the blade. The dermatome is provided with a handle by which the dermatome is maneuvered and advanced in the desired direction of the surface on which the skin may be cut, which handle is also used for actuating the knife in its reciprocating motion.

U.S. Pat. No. 3,428,045 is intended to be an improvement on the aforesaid U.S. Pat. No. 2,457,772. It is constituted by a frame, comprising a pair of opposite side members connected by a foot plate riding on the skin, a pressure plate mounted between the side members forwardly on the footplate, an oscillatory cutting element having its cutting edge forwardly off the foot plate and rearwardly off the pressure plate, for adjusting the pressure plate vertically for determining the depth of the cut, and assuring exact parallelism of the pressure plate with the forward edge of the foot plate. The dermatome further comprises means for actuating the blade in its oscillating movement. They are not described, and are stated to be any suitable means which form no part of the invention of the said patent. The width of the skin section to be taken is controlled by means of adjustable guide plates, one on either side of the dermatome, which underlie the blade and the foot plate and are slidably mounted on supporting rods. The dermatome is maneuvered by means of a handle which is fitted on an axial plane of the instrument, the plane being parallel to the motion of the dermatome and perpendicular to the blade edge.

DAS 2916268 describes a dermatome, characterized by the presence of swingable guide plates transversely juxtaposed of the cutting blade, which can be raised to expose the skin to the cutting blade or lowered to prevent contact of the skin with said blade. This patent does not describe a handle nor means for actuating the cutting blade. However, it does not have the features described in this application nor in the art, manufactured by Aesculap-Werke RG, the applicant of the aforesaid application, DAS 2916268, and they have a motor actuated cutting blade and a handle situated in an axial plane perpendicular to the cutting blade. The cut is limited in this dermatome, as well as in the dermatome described in the aforesaid DAS, by cutting elements located laterally of the cutting blade edges.

U.S. Pat. No. 4,690,139 is a hand-actuated dermatome with a guard for controlling the cutting depth and an adjusting mechanism for effecting an angular displacement between the guard and the cutting depth, the guard extending the complete length of the cutting edge of the blade and being rounded at its opposite end, enabling the full blade length to be used. The dermatome includes a handle which is offset from the plane on the head of which the cutting blade is mounted, and is pivoted from the first position overlying said head to a second position extending laterally of, but offset from, said head.

All the powered dermatomes known in the art have blades that are rather short (e.g., 10 cm of less), and thus the width of the incision and the resulting width of the graft is limited to narrow strips. The manual dermatomes have longer blades (more than 14–15 cm) with a resulting, potential, wide cutting front and wide graft. The dermatomes in which the blade is manually actuated are problematic. They require a considerable physical effort and technical skill on the part of the operator to produce a desired cutting, permit to use the central length of the blade in the cutting operation, except for the dermatome described in U.S. Pat. No. 4,690,139, in which the entire length and even the corners can be used. On the other hand, the dermatomes in which the blade is mechanically actuated may be much more efficient in their cutting operation but are so constructed that they can be advanced by pushing forward over the treated area of the skin substantially only in a direction perpendicular to the cutting blade, which makes it very difficult to operate over small skin areas or areas having a complex shape and renders the treated skin areas not as fully visible to the operator as they should be. Another drawback, common to all the dermatomes (except that of U.S. Pat. No. 4,690,139) is the geometry of the blades' ends, which are complex, have sharp angles, protrusions or ridges, and do not allow sidewise movement when the blade touches the skin.

Furthermore, said mechanically actuated dermatomes have sterility problems which exist practically in all surgical instruments which comprise an actuating electrical motor, and other electrical components, of non-stainless metals and other non-metallic materials. Absolute sterility of all the surgical instruments is required and any danger of pollution, no matter how minimal, must be avoided. For this purpose, the instrument is sterilized and is used in a completely sterile environment. However, the electrical motor, as well as the batteries, if it is battery-operated, cannot be subjected to the standard, "flash" autoclaving, sterilizing operation, which requires high temperatures and vapor pressures. For this reason most dermatomes are connected to a main electrical or gaz source by a flexible line. These lines cannot be autoclaved and should be gaz-sterilized, a method that demands time (24–48 hours) and means. It is possible, of course, to introduce the motor, and the batteries, if any, into the housing of the surgical instrument, which housing can be closed hermetically. However, contact between the non-sterilized motor and batteries can occur while it is introduced into the housing. Transitory contact of this kind is sufficient to destroy the absolute sterility that is required of the instrument and of the environment. In order to prevent this problem from arising, in one instrument (sold under the trade name Aesculap™) a separate plastic tunnel is provided to ensure a safe and non-contaminating passage of the non-sterile motor and batteries into the sterile housing. This tunnel has to be kept for use and discarded afterwards.

It is therefore a purpose of this invention to provide a mechanically-actuated dermatome which can be used over skin areas that are small or of complex shape.

It is another purpose of this invention to provide such a dermatome which allows the operator full visibility of the treated skin areas and access thereto.

It is a further purpose of this invention to provide such a dermatome which can be maneuvered by the operator most easily straight forward and sidewise, and with a minimum effort, on any skin surface.

It is a still further purpose of this invention to provide such a dermatome that can incise and excise tangentially very thin or thicker layers of skin or other tissues.

It is a still further purpose of this invention to provide a mechanically actuated dermatome that can be used as a hand actuated dermatome, in case of power failure.

It is a still further purpose of this invention to provide a surgical instrument, particularly but non exclusively a dermatome, comprising an electrical motor and/or batteries, which can be inserted into a housing, after the sterilization of the instrument, without in any way taking the risk of contamination of the sterilized instrument and therefore the sterile surgical environment and field.

It is a still further purpose of this invention to provide a surgical instrument that may be powered manually or by an electrical power pack that can be used and served by a single operator. For this requirement the operator, scrubbed, gowned and gloved, should be able to load, remove and reload the non-sterile, contaminated power pack into the sterile dermatome without breaking the operation room aseptic rules.

It is a still further purpose of this invention to provide a mechanically actuated dermatome that can excise as wide a front as in manually actuated dermatomes.

It is a still further purpose of this invention to provide an improved cutting instrument which can be maneuvered by the operator most easily and with a minimum effort.

Other purposes and advantages of the invention will appear as the description proceeds.

SUMMARY OF THE INVENTION

The dermatome according to the invention is a mechanically actuated dermatome, comprising a handle, to be gripped by the operator in order to control it, which handle is substantially perpendicular to the plane of the cutting blade. Said blade is a flat body and its upper and lower surface lie in parallel planes, and each of said planes, or any other plane parallel to them, can be considered as the cutting blade plane, for the purposes of defining the orientation of the handle.

Preferably, the blade and the mechanism actuating it in alternating motion are enclosed in a housing which has a lowermost surface that rides on the skin during treatment. Said lower surface is essentially parallel to the plane of the blade and the handle is substantially perpendicular to it and, of course, directly upwards when the dermatome rests on said lowermost surface of said housing.

The aforesaid, substantially perpendicular, orientation of the handle can be exactly determined if the handle is cylindrical or at least has circular cross-section, in which case the handle has a geometric axis and its orientation is that of said axis. If the handle does not have a geometric axis, then the general orientation that a hand assumes when it grips it to control the dermatome, will be considered as the orientation of the handle. Portions of the handle which the operator's hand does not contact when it controls the dermatome, will not be considered in determining the axis of the handle and in general its orientation. In general, only the part of the dermatome that is gripped by the operator when controlling the dermatome, is considered herein as being "the handle", and this term should be so construed in this specification and claims.

A perpendicular orientation of the handle permits the best control of the dermatome with the minimum effort.

Preferably, said blade housing and all other parts of the dermatome are so configured as to expose the ends of the blade, so that the dermatome may be slanted (if needed) by the operator to work on the skin only along a terminal portion thereof, adjacent to one of its ends.

According to another preferred embodiment of the invention, the blade housing is constructed in such a way that its entire underside (the one that comes in contact with the skin) is smooth, without any protrusions, sharp corners or any other obstacles to the reciprocated movement along its long axis against the skin. This feature is mandatory to allow the use of said dermatome as a manual dermatome.

According to another preferred embodiment of the invention, the two blades corners that are at the proximal and distal ends of the blades cutting front are hidden and protected from the skin by rounded protrusions, that are part of the base plate of the blade housing. In this embodiment, these two blades ends protectors differ what is disclosed in U.S. Pat. No. 4,690,139, of the present applicant, as in this latter the blade is stationary with respect to the housing and blades ends protectors, while in the dermatome of the present invention the blades slides in its reciprocal or continuous movement against and above these protectors and are different in size and design.

According to another preferred embodiment of the invention, the adjustable blade guard that determines the thickness of the excised tissue has rounded ends that surround the proximal and distal ends of the housing, thus facilitating the reciprocating or continuous movement of the entire housing and of the dermatome against the skin when used in its manual mode and its control in different than straight forward direction when used in its mechanically powered mode.

According to another, preferred feature of the invention, the dermatome handle, or the part of the dermatome that comprises the handle, as hereinbefore defined, is hollow and constitutes a housing for the motor, with or without batteries, which, in either case, constitutes what will be called "the power pack". Said housing is provided with a cover, removable to permit insertion of the power pack, but adapted to be applied to the handle to provide air-tight closure and to prevent contact of the non-sterile power pack with the environment and possible, consequent contamination. The batteries, when the motor is fed by batteries, may be housed in the same hollow handle or part comprising the handle, or in a separate battery housing connected to, but separate from, said handle, said separate housing being similarly provided with a removable cover, adapted to be applied to it to prevent contact of the batteries with the environment. A common cover may be provided, in this case, for both the motor and the battery housing. Said cover is provided with means for engaging the non-sterile power pack and means for engaging and close-locking into the housing. Both engaging-locking means can be operated remotely from the sterile surfaces by the scrubbed-sterile operator.

According to a more preferred feature of the invention, means are provided for preventing contact of the motor and the batteries—viz. the power pack—with the respective housings or with the common housing, when they are introduced into said housing or housings. Said means preferably comprise circumferential, hollow diaphragm or barrier means that are internally engaged by the motor and the batteries, if any, when the same are introduced into the housing or housings, and externally engage the inside of said housing or housings, thereby preventing contact of the former with the latter, said diaphragm means being introduced into said housing or housings, together with the motor and the batteries, and being isolated from the environment once the cover or covers are applied to the housing or housings. The shape of said diaphragm means is determined by the shape of the housing or housings with which they cooperate and with which they are structurally connected and/or of which they are a part. They are preferably sleeve-like bodies, made of thin metal plate, stainless or protected against rust and other surface contamination. Convenient metals are stainless steel, aluminum, titanium, etc. Said sleeve-like body can be replaced by a retractable guide (rod or rail) that extends above the housing level, is designed to engage the power-pack and guide its descent into the housing without touching any part of said housing.

It will be understood that said means for preventing motors and/or batteries, or any non-sterilizable parts that are required to be introduced into housings that are part of a surgical instrument, in order to operate the instrument, from contacting said housings, when they are introduced into them, can be used in any surgical instrument, besides a dermatome, to prevent contamination and assure complete sterility, and in such a case should be structured and shaped so as to be adapted to the surgical instrument. Therefore this invention comprises said contamination preventing means for application to any surgical instrument, a corresponding method for preventing contamination of surgical instruments, and any surgical instrument comprising said contamination preventing means.

Therefore the invention also comprises a device for preventing the contamination of sterilized surgical instruments into which non-sterilizable parts are to be introduced into housings of said instruments to operate them, which comprises diaphragm or barrier or a guiding mean engaged by the non-sterilizable parts, when the same are introduced into the housings, said diaphragm means being introduced into said housings, together with said non-sterilizable parts, and being isolated from the environment once covers are applied to said housings.

The invention further comprises a method for preventing the contamination of sterilized surgical instruments into which non-sterilizable parts are to be introduced into housings of said instruments to operate them, which comprises interposing diaphragm or barrier means between the non-sterilizable parts and the sterilized housings, when the said non-sterilizable parts are being introduced into said housings, and introducing said diaphragm means into said housings together with said non-sterilizable parts, and sealing said housings from the environment.

The invention further comprises sterile means for holding, removing or introducing the power pack into said diaphragm or the guide and the sterile housing. Said means may be part of the lid-cover that is designed to close hermetically the power pack housing. The actuating switch of the motor is situated on an accessible part of the handle and allows to turn on and off the motor without violation of the instrument external asepsis.

The invention further comprises means for an accurate tangential excision of thin or thicker layers of skin. These means are an exceptionally long amplitude (e.g. >6 mm) and a high (e.g. RPM>3500/min) of reciprocal movement of the blade compared to its housing when the power pack is used, or a continuous movement of a round, strip-like blade.

The invention also comprises a mechanically actuated cutting instrument intended for use in contact with the human skin, in particular a shaving instrument, having a cutting blade mechanically actuated in a reciprocating moton and power means for actuating it, and further comprising a handle, to be gripped by the operator in order to control it and to displace it over the surface to be treated, which handle is substantially perpendicular to the plane of the cutting blade, as defined with reference to dermatomes. Such a cutting instrument has essentially the same structure as the dermatome hereinbefore defined and described in detail hereinafter, and the features described with respect to the dermatomes apply to it as well, except that it will generally built on a smaller scale, adapted to its use, and generally may not be required to be completely sterile. Obviously, it will be used in an appropriate manner, viz. it will be caused to slide over the skin without applying such pressure as would cause it to cut into it.

DETAILED DESCRIPTION OF PREFERRED EMBODIMENTS

In the embodiment of FIGS. 1 to 4, the dermatome comprises a blade housing generally designated at 10 and a handle generally designated at 11, which is also a motor and batteries housing. Blade housing 10 also houses a mechanism for supporting and driving the blade, particularly illustrated in FIG. 4. The blade is indicated by numeral 31. The blade holder 12 has extensions 13 and 13a, which are connected to knobs 14 and 14a mounted on pins 15 and 15a, which are slidably mounted in supports 16 and 16a and are urged away from said supports by compression springs 17 and 17a. Pin 18 is pivotedly connected at 18 to a connecting rod 19, which is in turn pivoted to an eccentric actuated for rotation by a motor 22. In the embodiment illustrated, the eccentric is constituted by a pin 20 eccentrically connected to the motor shaft 23 and rotating with it. Motor 22 is powered by batteries 24 and both motor and batteries are housed in handle 11. It should be noted that the means for driving blade 31 and blade holder 12 in alternating motion are only an example, as many other known kinematisms may be provided for producing said motion, without departing from the invention.

Handle 11 is rigidly connected to blade housing 10, at or near one end thereof, as is indicated generally at 25, and is provided in enlarged upper portion 26 for housing the batteries 24, with a central body 28 having a diameter suitable for housing motor 22, and with an airtight cover 27, 27' indicates a cover handle, that is preferably provided for lifting the cover and triggers to engage/release the power pack and locks to engage/release the handle, by means of any suitable, generally spring-biased locking means. A guard 30, made of a rod bent in a U-shape, is provided above the blade holder 12 and protrudes slightly beyond the cutting edge of the blade 31 (see FIG. 2B).

Figure 5A:
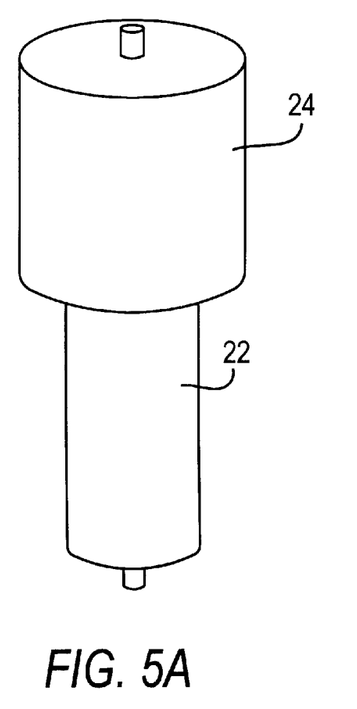
FIGS. 5A and 5B are perspective views illustrating the means for introducing the power pack into the sterilized housing of the dermatome of FIGS. 1 to 4.
Figure 5B:
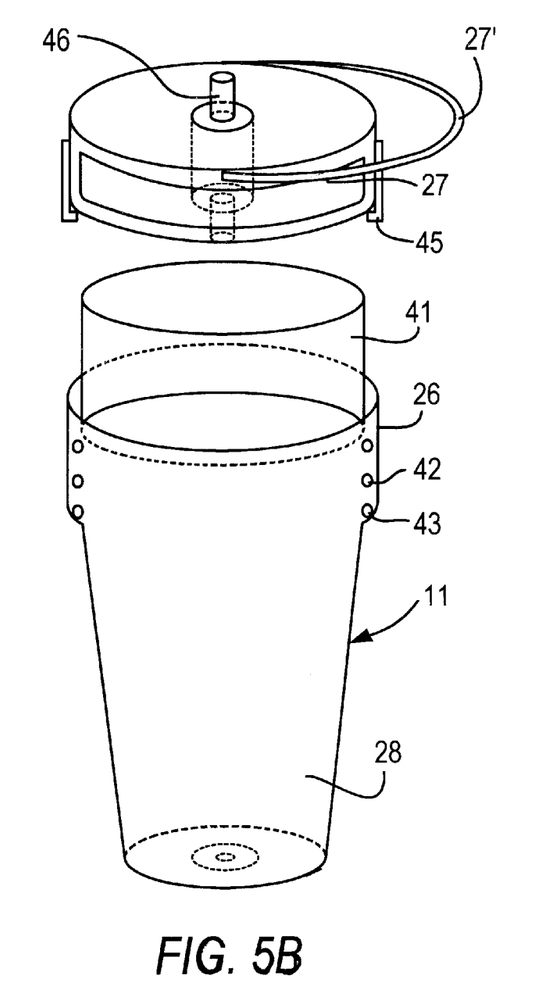

In order to introduce the motor and the batteries into their respective housings, without causing contamination to the dermatome and therefore to the sterile environment, a cylindrical diaphragm constituted by a protecting sleeve 41 is provided (see FIGS. 5A–5B). It has an outer diameter that is slightly smaller than the inner diameter of the upper portion 26 of the handle.

The operation of the protective sleeve 41 is schematically illustrated in FIGS. 5B. The body of the dermatome, without motor and without batteries, has been sterilized and is in an open condition, its sterile cover being separated from it. The power pack (FIG. 5A), comprises batteries and motor 22, which, in this embodiment are vertically aligned and disposed the first above the second. The protective sleeve 41 has an inner diameter corresponding to the outer diameter of the batteries 24. It is urged upwards by spring 42, so as to project from the opening of the handle, viz. from the edge of upper portion 26. Spring 42 abuts with it upper end on the lower edge of sleeve 41 and with its lower end on the inside of handle 11 at plane 43 where said upper portion 26 ends, viz. where at the upper end of a conical restriction 44 that joins said upper portion to handle body 28. The power pack 24-22 is introduced into handle 11 through sleeve 41, and in this operation, the batteries entrain the protective sleeve 41 into the upper portion 26 of the handle, compressing spring 43 and lowering the top portion of sleeve 41 below the edge of said portion 26. In its motion, the protective sleeve slides over the inner surface of the housing and prevents the motor or batteries from coming into contact with it. The motor and batteries reach the position in which they must be in the assembled dermatome, the batteries abutting on the handle inner surface on plane 43; and the pin 20, eccentrically carried by the motor shaft, comes into engagement with connecting rod 19. In that position, the sleeve is entirely within the handle, or at least within the space enclosed by the handle and its cover 27. A gasket 45 is preferably provided to create a tight seal between the cover and the handle. The cover is also provided with means for locking it into the handle with or without the power pack and with means for locking onto the power pack, without contaminating the external sterile surface of the dermatome, said means being schematically indicated at 46 Provision of said means allows a single operator, scrubbed, gowned and gloved, to handle the sterile dermatome, loading and replacing the non-sterile, contaminated power pack without disrupting the operating room aseptic operation field rules. A lever (not shown) is provided to actuate from the outside the electrical switch of the power pack.

Figure 1:
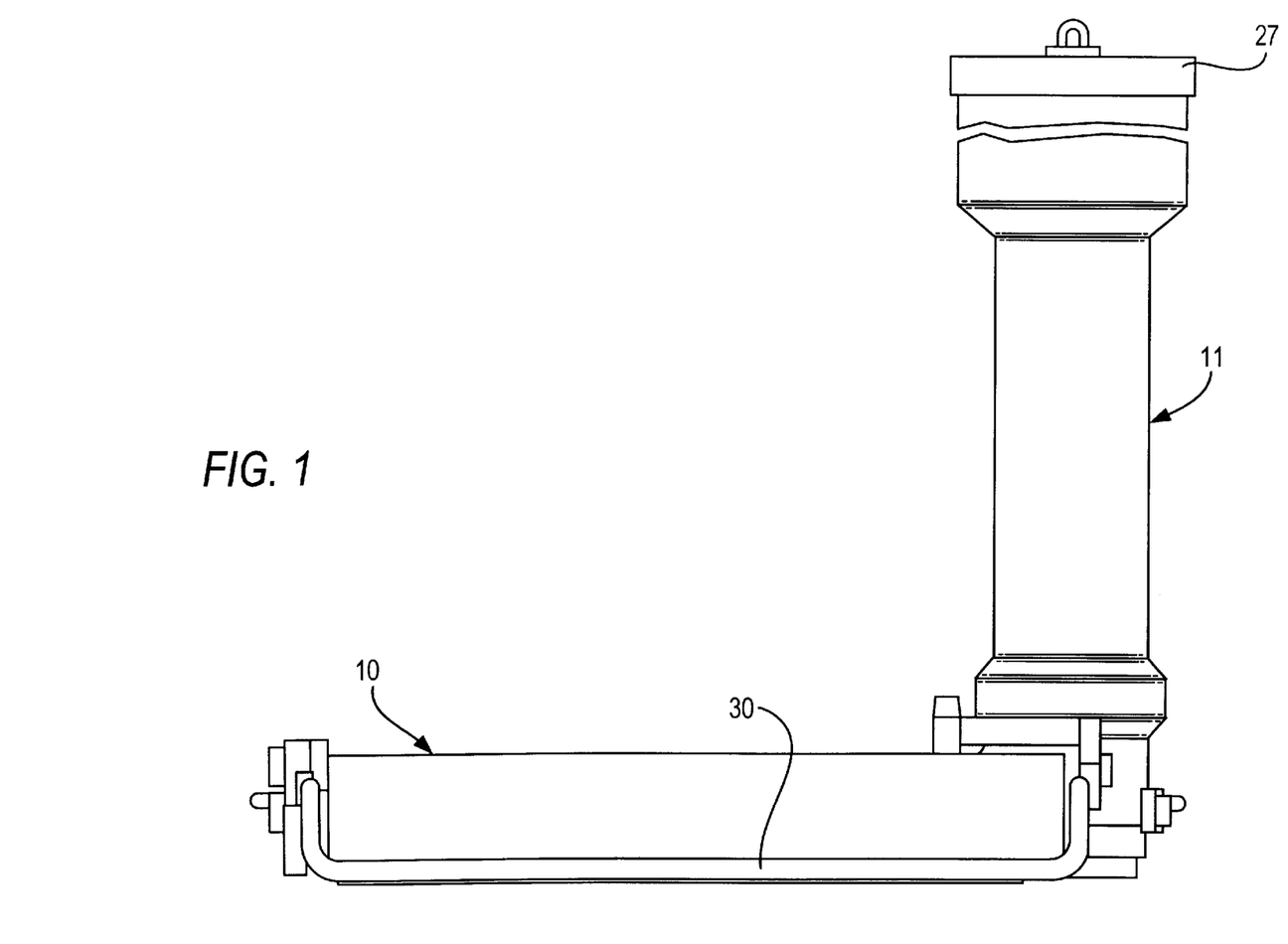
FIG. 1 is a front view of a dermatome according to a first embodiment of the invention.
Figure 2A:
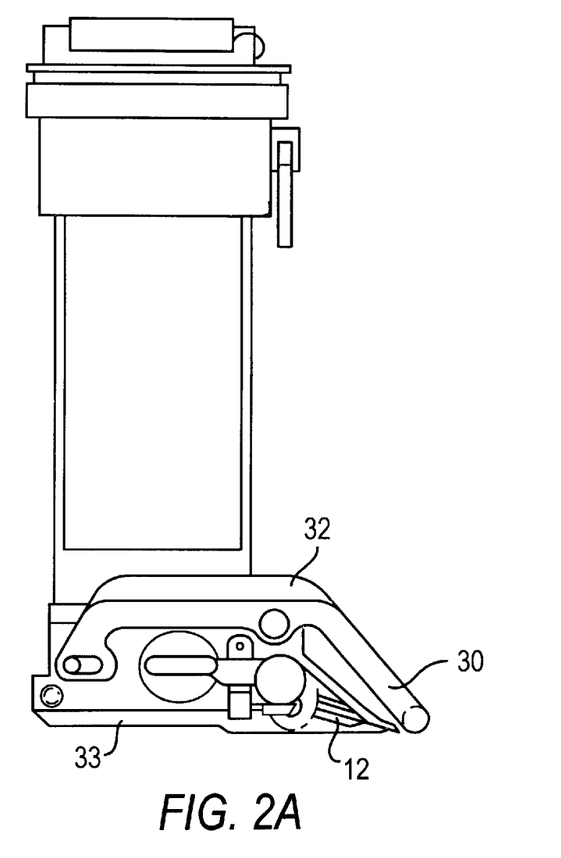
FIG. 2A is an end view of the same dermatome and FIG. 2B is a detail of FIG. 2A showing, at an enlarged scale, the blade housing and related mechanical parts.
Figure 2B:
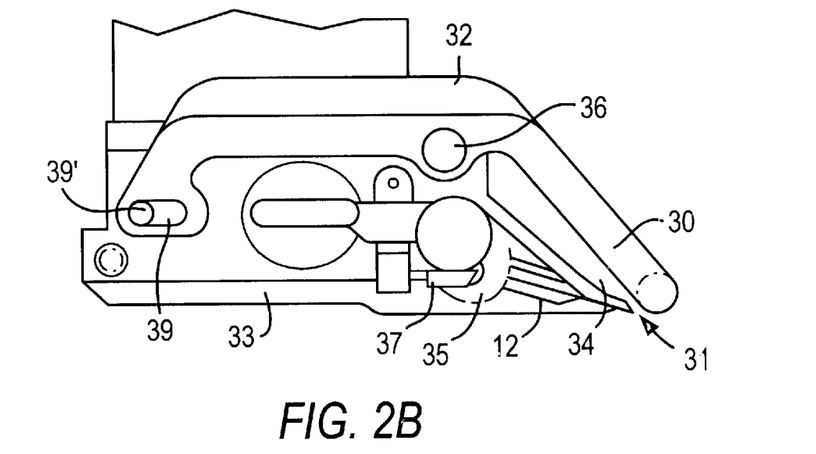
Figure 3:
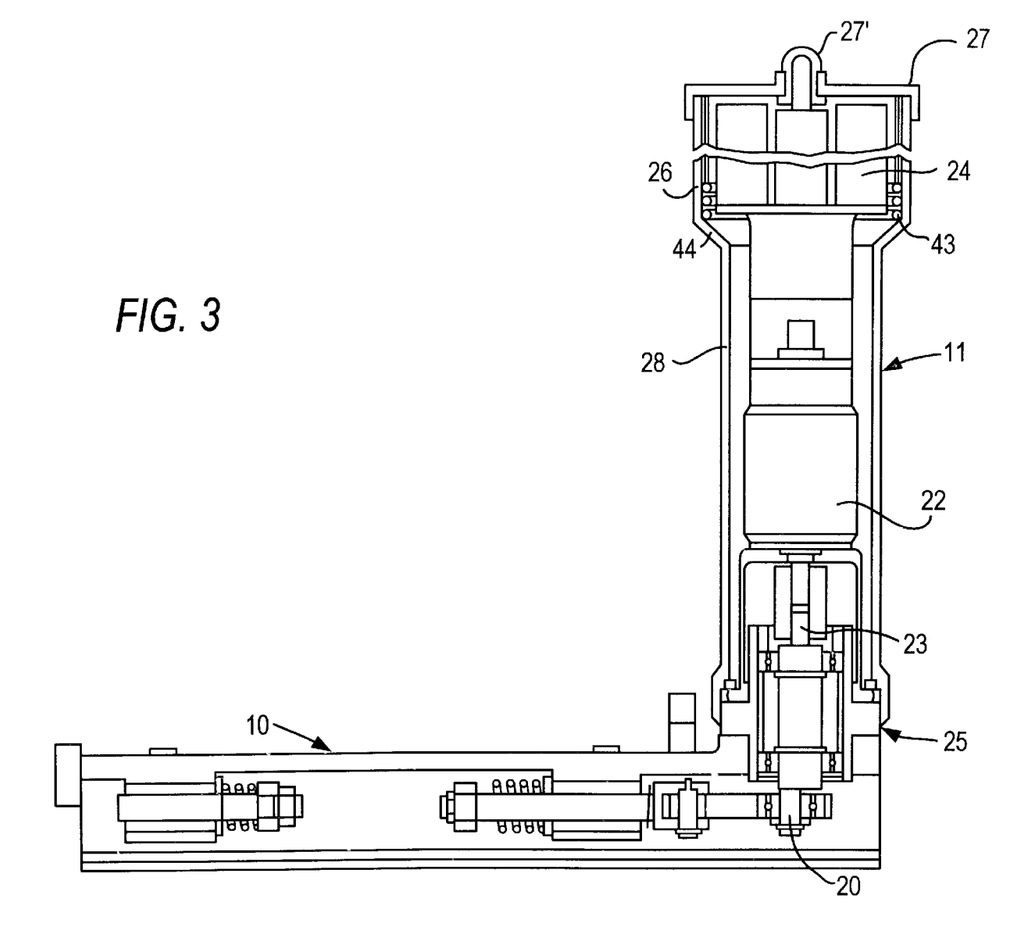
FIG. 3 is a vertical cross-section of the same dermatome, taken on plane III—III of FIG. 24, showing the inner mechanisms in view.
Figure 4:
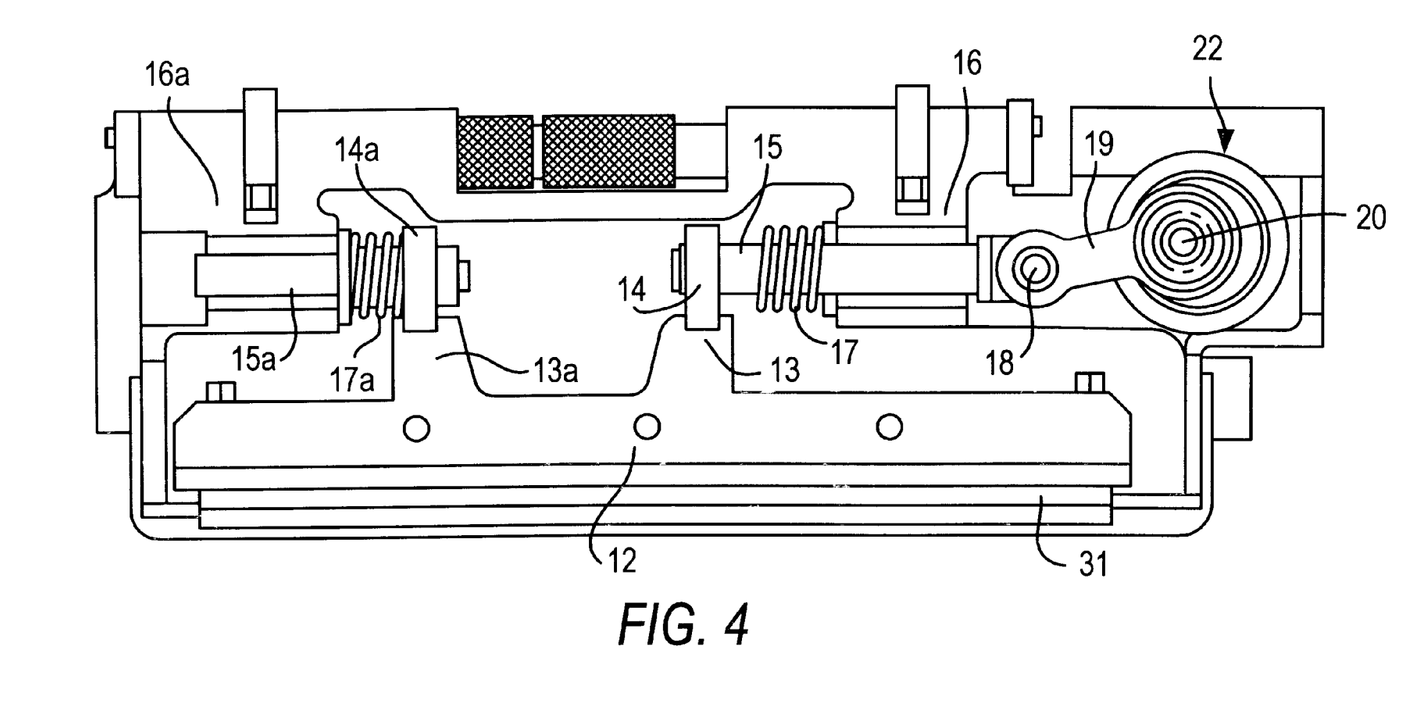
FIG. 4 is a plan view of the same dermatome from the bottom, with the bottom cover removed to show the blade actuating mechanism.

The blade housing 10 is composed of an upper portion or top plate 32 and a lower portion or bottom plate 33, which leave, in the forward edge of the housing, a gap indicated at 34, from which the blade 31 projects. As best seen in FIG. 2B which is a partial end view of the dermatome of this embodiment, showing only the blade housing and associated parts, a hook 35 engages a projection 37 of the lower portion 33 to fix it in an operative position. A similar hook is provided at the other end of the dermatome, and is not seen in FIG. 2B. The blade guard 30 is pivoted at 36 to the upper portion 32 of the blade housing. A slit 39, engaged by a pin 39', permits to regulate the blade guard according to the need of specific operations. Other means may be provided for locking the lower portion of the housing to its main body.

Figure 6:
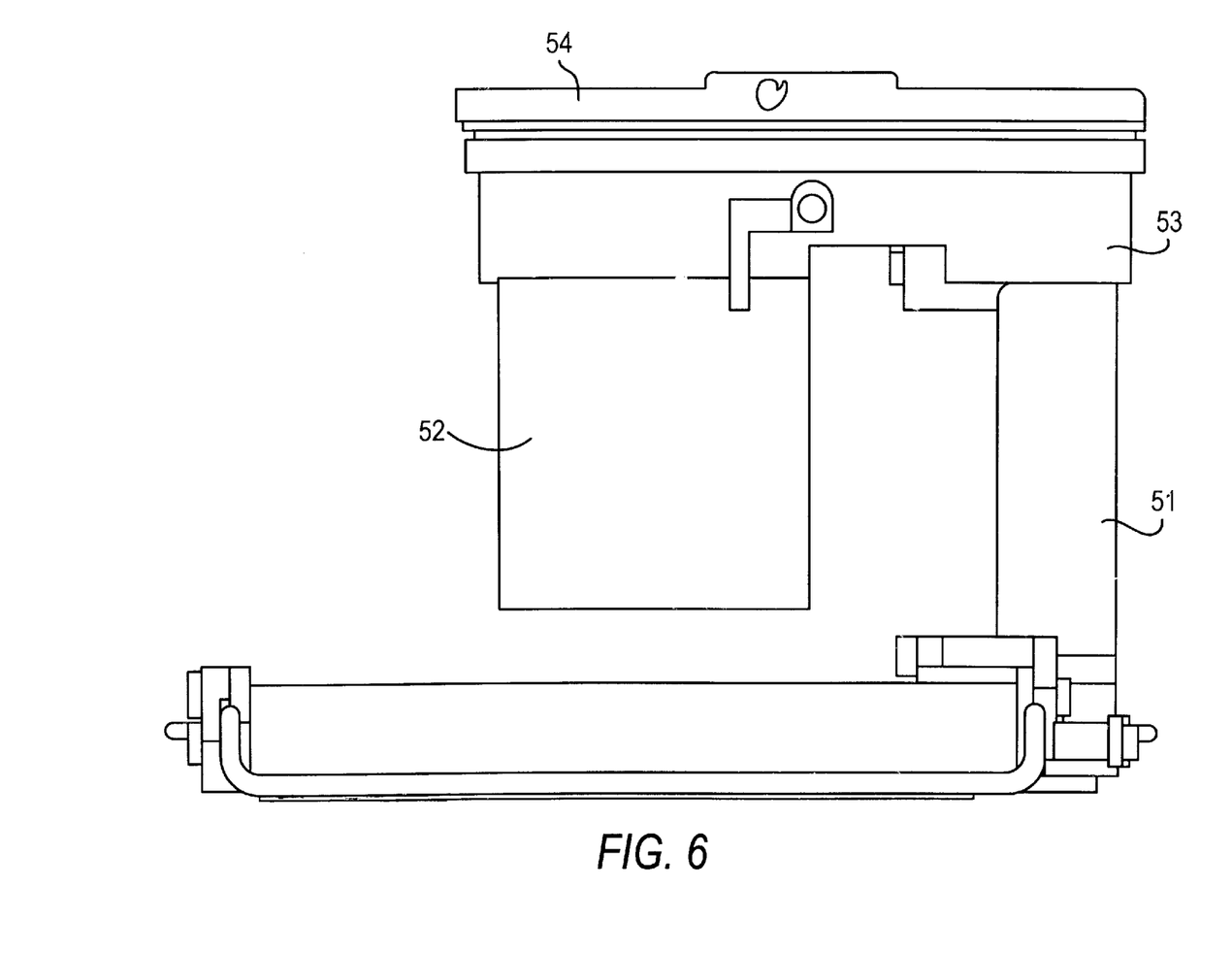
FIG. 6 is a front view of a dermatome according to a second embodiment of the invention.
Figure 7:
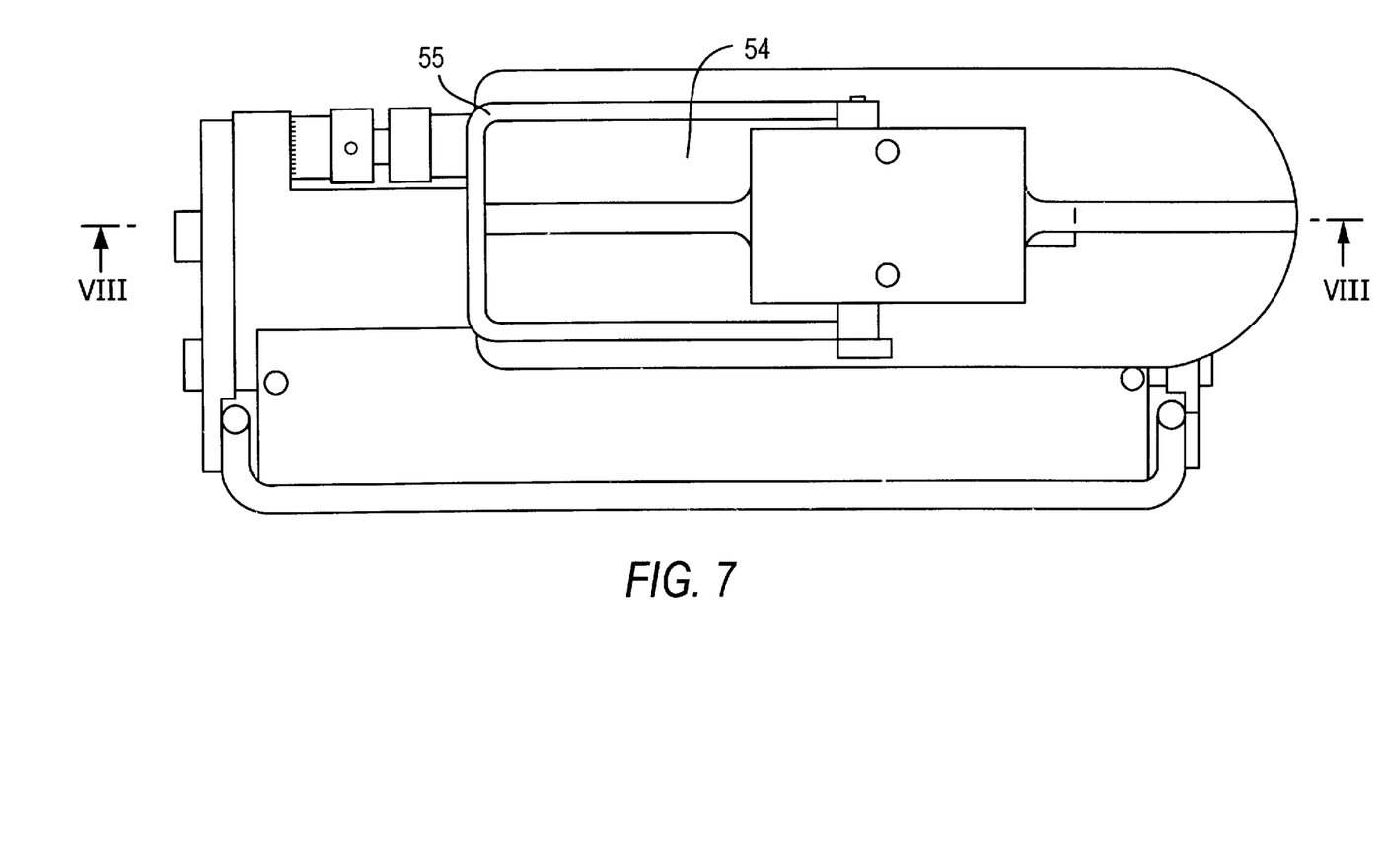
FIG. 7 is a top view of the same.
Figure 8:
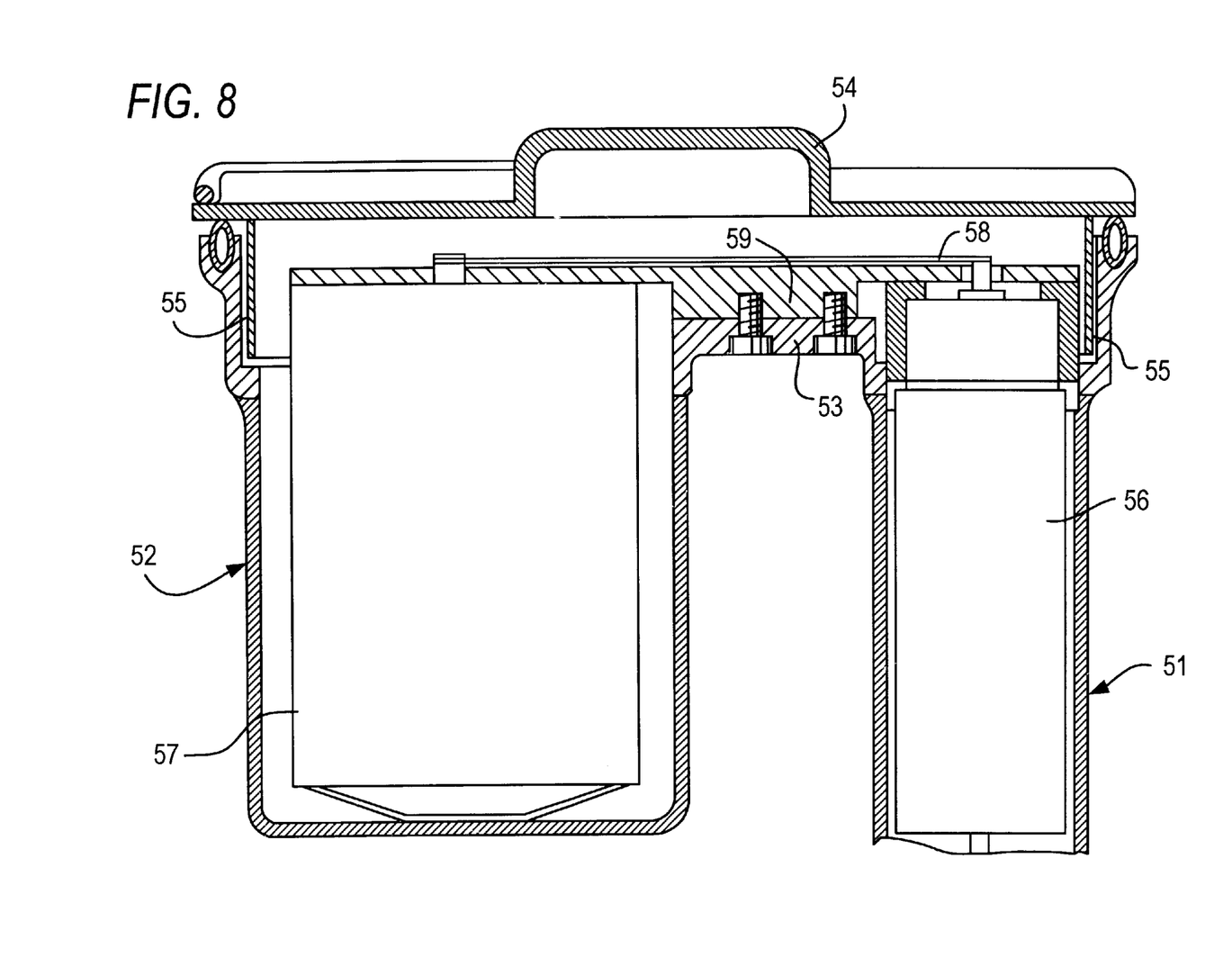
FIG. 8 is a partial vertical cross-section of the same on plane VIII—VIII of FIG. 7.
Figure 9:
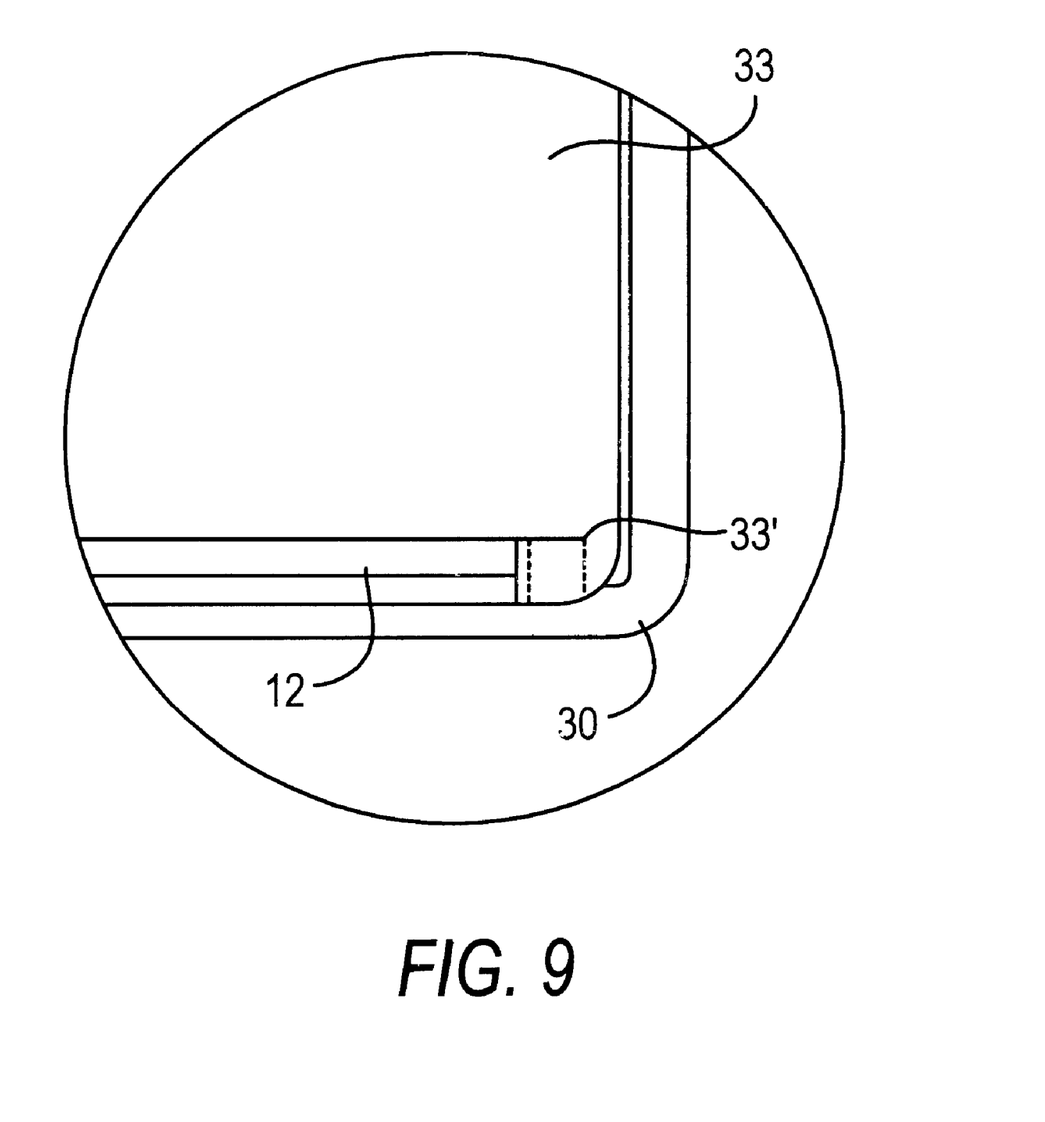
FIG. 9 is a detail showing in plan view from the bottom a corner of the blade and adjacent parts of an embodiment of a dermatome according to the invention.

As seen in FIG. 9, blade guard 30, which extends the whole length of the blade 31, is rounded at its ends, to enable the full length of the blade to be used. The bottom plate 33 is provided at its ends with projections 33', which prevent the blade corners from catching against the skin during operation of the dermatome. A second embodiment of the invention is illustrated in FIGS. 6, 7, and 8. The blade housing and the mechanism for actuating the blade are the same as those in the first embodiment and can be considered as illustrated by FIGS. 2A, 2B, 3, and 9. As far as shown, the parts of said housing and mechanism are indicated by the same numerals as used to describe the first embodiment. However, this embodiment has a handle 51, which houses only the motor, the batteries being housed in a battery housing 52. The two housings are connected by a bridge 53. They are covered by a common cover 54, having a handle 55 for lifting it. In order to introduce the motor and batteries into their respective housings, after sterilizing the dermatome, without causing contamination, a diaphragm constituted by a protective sleeve 55 is provided. It operates in the same way as sleeve 41, described in connection with the first embodiment, but has an elongated shape, so as to be engaged concurrently by the motor 56 and batteries 57 in order to introduce them into handle 51 and battery housing 52, once these have been sterilized, without contamination.

FIG. 8 is a cross-section of the battery and the motor housing, this latter broken off at the level of the bottom of the battery housing. As seen therein, electrical wires 58 are provided to carry power from the batteries to the motor. An inner bridge 59 carries the battery pack 57 and the motor 56, as well as the said wires 56, all of said parts being attached thereto in any convenient way, not illustrated. Said bridge 57 can be attached to the cover or removed therefrom by any suitable means, such as hooks, not illustrated, since they may be of any convenient structure, easily designed by expert persons, so that the entire assembly constituted by the battery pack and the motor and attached parts can be lifted by lifting of said cover.

While examples of the invention have been given by way of illustration, it will be apparent that many modifications, variations and adaptations may be made therein by persons skilled in the art, without departing from the spirit of the invention or exceeding the scope of the claims.

What is claimed is:

1. Mechanically actuated dermatome, comprising a cutting blade having a cutting edge, a motor and transmission means for imparting to said blade an alternating motion parallel to said cutting edge, said dermatome further comprising a handle a handle to be gripped by the operator in order to control the displacement of the dermatome concurrently with said alternating motion of said blade, wherein said handle is perpendicular to the plane of said cutting blade such that the displacement of the dermatome will be substantially perpendicular to said cutting edge, batteries for feeding said motor, and which further comprises a motor battery housing connected to but separated from said handle, said separate housing being provided with a removable cover, adapted to be applied to it to prevent contact of said batteries with the environment.

2. Mechanically actuated dermatome, comprising a cutting blade, a mechanism for driving said cutting blade, and a handle to be gripped by the operator to control the displacement of the dermatome, said handle being perpendicular to the plane of said cutting blade, said dermatome further comprising a circumferential, hollow diaphragm structurally connected with the dermatome handle and having such dimensions as to be internally engageable by a power pack sized to fit into the dermatome handle, and spring means for urging said diaphragm to project from said dermatome handle, whereby when said power pack is introduced into said handle, it entrains said diaphragm, said diaphragm being interposed between said power pack and said handle and being isolated from the environment once the cover or covers are applied to said housing or housings.

3. Mechanically actuated dermatome comprising a cutting blade, a mechanism for imparting to said cutting blade an alternating motion, said mechanism comprising a motor fed by batteries, and a handle to be gripped by the operator in order to control the displacement of the dermatome, said handle being perpendicular to the plane of said cutting blade, said dermatome further comprising a circumferential, hollow diaphragm structurally connected with the dermatome handle and battery housing, said diaphragm having such dimensions as to be internally engageable by said motor and said batteries and as to fit into handle and housing, whereby when said motor and batteries are introduced into the dermatome, they entrain said diaphragm, said diaphragm being interposed between said motor and batteries and said handle and battery housing respectively, and being isolated from the environment once the cover is applied to said handle and battery housing.

4. Surgical instrument comprising a housing or housings for at least a motor and/or batteries and a cover and further comprises means for preventing contamination of the instrument by preventing contact of motors and/or batteries with their housings, when they are introduced into said housings, which contamination preventing means comprise a hollow diaphragm structurally connected with said housing or housings, said diaphragm having such dimensions as to be internally engageable by said motor and/or batteries and as to fit into said housing or housings, whereby when said motor and/or batteries are introduced into the surgical instrument, they entrain said diaphragm, said diaphragm being interposed between said motor and/or batteries and said housing or housings, and being isolated from the environment once said cover is applied to said housing or housings.

5. Surgical instrument as defined in claim 4 wherein said instrument is not a dermatome.

* * * * *